United States Patent [19]
Gall et al.

[11] Patent Number: 4,927,814
[45] Date of Patent: May 22, 1990

[54] DIPHOSPHONATE DERIVATIVES, PHARMACEUTICAL COMPOSITIONS AND METHODS OF USE

[75] Inventors: Rudi Gall, Hirschberg; Elmar Bosies, Weinheim, both of Fed. Rep. of Germany

[73] Assignee: Boehringer Mannheim GmbH, Mannheim, Fed. Rep. of Germany

[21] Appl. No.: 71,471

[22] Filed: Jul. 9, 1987

[30] Foreign Application Priority Data

Jul. 11, 1986 [DE] Fed. Rep. of Germany ....... 3623397

[51] Int. Cl.$^5$ .......................... C07F 9/38; A61K 31/66
[52] U.S. Cl. .................................... 514/108; 558/158; 562/13
[58] Field of Search ................ 558/158; 260/502.5 C; 514/108; 562/13

[56] References Cited

U.S. PATENT DOCUMENTS

| | | | |
|---|---|---|---|
| 3,733,270 | 5/1973 | Kerst | 210/58 |
| 3,962,432 | 6/1976 | Schmidt-Dünker | 514/108 |
| 4,054,598 | 10/1977 | Blum et al. | 260/502.5 C |
| 4,134,969 | 1/1979 | Schmidt-Dunker | 260/502.5 C |
| 4,327,039 | 4/1982 | Blum et al. | 260/502.5 C |
| 4,621,077 | 11/1986 | Rosini et al. | 514/108 |
| 4,624,947 | 11/1986 | Blum et al. | 562/13 |

FOREIGN PATENT DOCUMENTS

| | | |
|---|---|---|
| 0096931 | 12/1983 | European Pat. Off. . |
| 0175315 | 3/1986 | European Pat. Off. . |
| 3623397 | 1/1988 | Fed. Rep. of Germany . |
| 2259615 | 8/1979 | France . |
| 739076 | 6/1980 | U.S.S.R. . |
| 1254465 | 11/1971 | United Kingdom . |

Primary Examiner—Anton H. Sutto
Attorney, Agent, or Firm—Felfe & Lynch

[57] ABSTRACT

The present invention provides disphosphonates of the general formula:

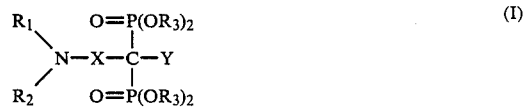

wherein $R_1$ is a straight-chain or branched, saturated or unsaturated aliphatic hydrocarbon radical of 1-9 carbon atoms which is optionally substituted by phenyl or cyclohexyl, $R_2$ is cyclohexyl or cyclohexylmethyl, benzyl or a straight-chained or branched, saturated or unsaturated aliphatic hydrocarbon of 4 to 18 carbon atoms which is optionally substituted by phenyl or oxygen wherein the oxygen can be esterified or etherified, $R_3$ is hydrogen or a straight-chain or branched alkyl of 1-4 carbon atoms, X is a straight-chain or branched alkylene chain of 1-6 carbon atoms and Y is hydrogen, hydroxyl or an amino group optionally substituted by alkyl radicals of 1-6 carbon atoms; as well as the pharmacologically acceptable salts thereof.

The present invention also provides processes for the preparation of these diphosphonic acid derivatives and pharmaceutical compositions containing them for the prophyllaxis treatment of diseases or disturbances of calcium metabolism such as osteoporsis, Pagets disease, Bechterew's disease, bone metastases, urolithiasis, heterotropic ossifications, rheumatoid arthritis, osteoarthritis and degenerative arthrosis.

12 Claims, No Drawings

DIPHOSPHONATE DERIVATIVES, PHARMACEUTICAL COMPOSITIONS AND METHODS OF USE

The present invention is concerned with new diphosphonic acid derivatives, processes for the preparation thereof and pharmaceutical compositions containing them.

Federal Republic of Germany Patent Specification No. 18,13,659 describes diphosphonic acid derivatives, of which 1-hydroxyethane-1,1-diphosphonic acid has achieved importance as an agent for the treatment of Paget's disease. Belgian Patent Specification No. 896,453, Federal Republic of Germany Patent Specification No. 25,34,391 and European Patent Specification No. 0,096,931 described aminoalkane-1,1-diphosphonic acids as good calcium complex formers which can also be used for the treatment of increased bone resorption. However, in the case of therapeutically effective dosages, such compounds frequently display side effects.

Consequently, there is a need to provide new aminoalkane-diphosphonates which manifest a therapeutic effectiveness at the lowest possible dosage level.

We have now found that analogous derivatives of these compounds in which the nitrogen atom is completely alkylated, the alkyl radical thereby containing at least 4 carbon atoms, fulfil this requirement and can be used as good calcium complex formers for the broader treatment of calcium metabolism disturbances. In particular, they can be well used where the bone formation and breakdown is disturbed, i.e. they can be used for the treatment of diseases of the skeletal system, for example osteoporosis, Paget's disease, Bechterew's diseases and the like.

However, on the basis of these properties, they can also be used for the therapy of bone metastases, urolithiasis and for the prevention of heterotopic ossifications. Due to their influence on calcium metabolism, they also form a basis for the treatment of rheumatoid arthritis, osteoarthritic and degenerative arthrosis.

Thus, according to the present invention, there are provided diphosphonates of the general formula:

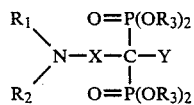

wherein $R_1$ is a straight-chained or branched, saturated or unsaturated aliphatic hydrocarbon radical containing up to 9 carbon atoms which is optionally substituted by phenyl or cyclohexyl radicals, $R_2$ is a cyclohexyl or cyclohexylmethyl radical, a benzyl radical or a straight-chained or branched, saturated or unsaturated alkyl radical containing 4 to 18 carbon atoms which is optionally substituted by phenyl radicals or oxygen, which can be esterified or etherified, $R_3$ is a hydrogen atom or a straight-chained or branched alkyl radical containing up to 4 carbon atoms, X is a straight-chained or branched alkylene chain containing up to 6 carbon atoms and Y is a hydrogen atom, a hydroxyl group or an amino group optionally substituted by alkyl radicals containing up to 6 carbon atoms, as well as the pharmacologically compatible salts thereof.

The substituent $R_1$ is preferably a methyl, n-propyl, isopropyl, 3-methylbutyl, pentyl or nonyl radical.

$R_2$ is preferably a butyl, isobutyl, 3-methylbutyl, pentyl, heptyl, nonyl, decyl, undecyl, dodecyl, tetradecyl, hexadecyl, octadecyl, cyclohexyl, cyclohexylmethyl or benzyl radical.

The ethers and esters which can be formed with the oxygen in the case of the substituent $R_2$ mean alkyl- or alkyl-CO radicals containing up to 18 and preferably 9 to 18 carbon atoms, the nonyloxy, tetradecyloxy, hexadecylcarbonyloxy and octadecylcarbonyloxy radicals being preferred.

The substituent $R_3$ is preferably a hydrogen atom or a methyl, ethyl or isobutyl radical.

The asymmetrical carbon atoms occurring in $R_1$, $R_2$ and X can have the R-, S- or R,S-configuration.

The group X is preferably an ethylene, propylene, butylene, 1-methylpropylene, 2-methylpropylene, 1-methyl-butylene or 2-methylbutylene radical.

The group Y is preferably a hydrogen atom, a hydroxyl group or an amino group which can be substituted by methyl, ethyl or isopropyl.

Preferred compounds of general formula (I) according to the present invention are those in which $R_1$ is a methyl radical and $R_2$ is a $C_4$–$C_6$ radical, especially the compounds 1-hydroxy-3-(N-methyl-N-pentyl-amino)-propane-1,1-diphosphonic acid and 1-hydroxy-3-(N-isobutyl-N-methylamino)-propane-1,1-diphosphonic acid.

The compounds of general formula (I) according to the present invention can be prepared by known processes:

I. For the case in which Y in general formula (I) represents a hydrogen atom, the compounds are preferably prepared as follows:

(a) a compound of the general formula:

wherein $R_1$, $R_2$ and X have the above-given meanings and B is a reactive residue, for example a halogen atom or a sulphonate group, is reacted with a compound of the general formula:

wherein R' is an alkyl radical containing up to 4 carbon atoms, preferably a methyl, ethyl or isobutyl radical, to give a diphosphonate of the general formula:

wherein $R_1$, $R_2$, X and R' have the above-given meanings, and the resultant tetraester is optionally saponified to the corresponding diester or free acid of general formula (I); or (b) a compound of the general formula:

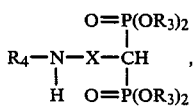  (V)

wherein $R_3$ and X have the above-given meanings and $R_4$ is a hydrogen atom or has the same meaning as $R_2$, is mono- or dialkylated and the resultant tetraester is optionally saponified to the corresponding diester or free acid of general formula (I); or II. for the case in which Y in general formula (I) is an amino group optionally substituted by alkyl radicals, a carboxylic acid derivative of the general formula:

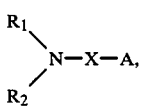  (VI)

wherein $R_1$, $R_2$ and X have the above-given meanings and A is a nitrile or imino ether group or a carboxamide group optionally substituted on the nitrogen atom by a lower alkyl radical, is reacted with a phosphorus compound of the general formula:

$$PT_3 \qquad (VII)$$

wherein T is a halogen atom, a hydroxyl group or an OR' group, R' having the above-given meaning, and optionally subsequently saponified to give a compound of general formula (I); or III. for the case in which Y in general formula (I) is a hydroxyl group, (a) a carboxylic acid of the general formula:

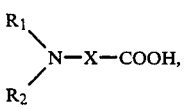  (VIII)

wherein $R_1$, $R_2$ and X have the above-given meanings, is reacted with a mixture of phosphorous acid or phosphoric acid and a phosphorus halide and subsequently saponified to a free diphosphonic acid of general formula (I); or (b) a carboxylic acid chloride of the general formula:

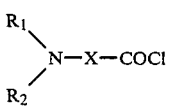  (IX)

wherein $R_1$, $R_2$ and X have the above-given meanings, is reacted with a trialkyl phosphite of the general formula:

$$P(OR')_3 \qquad (X)$$

wherein R' has the above-given meaning, to give an acyl phosphonate of the general formula:

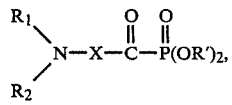  (XI)

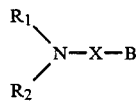  (II)

wherein $R_1$, $R_2$, X and R' have the above-given meanings, subsequently reacted with a dialkyl phosphite of the general formula:

  (XII)

wherein R' has the above-given meaning, to give a diphosphonate of the general formula:

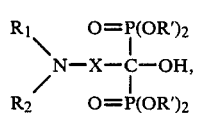  (XIII)

wherein $R_1$, $R_2$, X and R' have the above-given meanings, and the resultant tetraester is optionally saponified to the corresponding diester or free acid of general formula (I); or (c) a compound of the general formula:

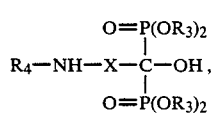  (XIV)

wherein $R_3$ and X have the above-given meanings and $R_4$ is a hydrogen atom or has the same meaning as $R_2$, is mono- or dialkylated and the resultant tetraester is optionally saponified to the corresponding diester or free acid of general formula (I); and, if desired, the compounds thus prepared are converted into their pharmacologically compatible salts.

In the case of process I (a), the methylene-diphosphonic acid ester of general formula (III) is used in the form of its sodium or potassium salt. For this purpose, it is reacted with sodium, potassium or the appropriate hydride in an inert solvent, for example benzene, toluene or dimethylformamide, at a temperature of from 0° to 40° C. and preferably of 25° C. The alkali metal salt is, without isolation, reacted with an appropriate halide or sulphonate, the temperature used hereby being from 20° to 110° C.

In the case of the reductive alkylation according to process I (b), a mixture of primary or secondary amine of general formula (V) and of a carbonyl compound or of an acetal thereof is treated in the presence of a hydrogenation catalyst, for example palladium on charcoal or nickel, with hydrogen at atmospheric or increased pressure or with the use of formic acid as reducing agent. Subsequently, alkylation of a secondary amine of general formula (V) can be carried out especially advantageously according to the phase transfer process with dialkyl sulphates.

In the case of process II, the nitriles of general formula (VI) are reacted with phosphorous acid at a temperature of from 110° to 180° C. The reaction can be carried out without or in the presence of aprotic solvents, for example diglycol dimethyl ether or diglycol diethyl ether. However, the nitriles can also be reacted with a phosphorus trihalide, for example phosphorus tribromide or phosphorus trichloride, in an inert solvent, for example dioxan or tetrahydrofuran, optionally with the addition of water, at a temperature of from 20° to 80° C. Imino ethers of general formula (VI) are preferably reacted with dialkyl phosphites in the presence of equimolar amounts of sodium in inert solvents, for example diethyl ether, dioxan or also benzene, the reactions usually taking place at the reflux temperature of the solvent used. Acid amides of general formula (VI) can be reacted in inert solvents, for example halogenated hydrocarbons or ethers, such as diethyl ether, with a mixture of a phosphorus pentahalide/phosphorous acid or also of oxalyl chloride/trialkyl phosphite.

The carboxylic acids of general formula (VIII) used in process III (a) are reacted with 1 to 2 and preferably 1.5 mole phosphorous acid or phosphoric acid and 1 to 2 and preferably 1.5 mole phosphorus trihalide at a temperature of from 80° to 130° C. and preferably of from 100° to 110° C. The reaction can also be carried out in the presence of diluents, for example halogenated hydrocarbons, especially chlorobenzene or tetrachloroethane, or also dioxan. The subsequent hydrolysis takes place by boiling with water but preferably with semiconcentrated hydrochloric or hydrobromic acid.

In the case of process III (b), the acid chloride of general formula (IX) is reacted with the trialkyl phosphite of general formula (X) at a temperature of from 0° to 60° C. and preferably of from 20° to 40° C. The reaction can be carried out without a solvent or also in the presence of inert solvents, for example diethyl ether, tetrahydrofuran, dioxan or also halogenated hydrocarbons, for example methylene chloride. The acyl phosphonate of general formula (XI) formed as intermediate can be isolated or further reacted directly. The subsequent reaction is carried out in the presence of a weak base, preferably of a secondary amine, for example dibutylamine, at a temperature of from 0° to 60° C. and preferably of from 10° to 30° C.

As phosphorus trihalides in the above-mentioned processes, there can be used, for example, phosphorus trichloride or phosphorus tribromide.

In the case of process III (c), there applies analogously the remarks made with regard to process I (b).

The tetraalkyl esters possibly obtained in processes I and III can be saponified to the corresponding diesters or to the free tetra acids. The saponification to diesters usually takes place by treating the tetraalkyl esters with an alkali metal halide, preferably sodium iodide, in an appropriate solvent, for example acetone, at ambient temperature. There is hereby obtained the symmetrical diester/disodium salt which, if desired, can be converted into the diester/diacid by means of an acidic ion exchanger. The saponification to the free diphosphonic acids usually takes place by boiling with hydrochloric or hydrobromic acid. However, a cleavage with a trimethylsilyl halide, preferably the bromide or iodide, can also be carried out. On the other hand, the free diphosphonic acids can be converted again into the tetraalkyl esters by boiling with orthoformic acid alkyl esters. The free diphosphonic acids of general formula (I) can be isolated as the free acids or in the form of their mono- or dialkali metal salts. The alkali metal salts can usually be readily purified by reprecipitation from water/methanol or from water/acetone.

As pharmacologically acceptable salts, there are preferably used the alkali metal or ammonium salts which can be prepared in the usual way, for example by titration of the compounds with inorganic or organic bases, for example sodium or potassium hydrogen carbonates, aqueous solutions of sodium or potassium hydroxide or aqueous solutions of ammonia or of amines, for example trimethyl or triethylamine.

The new compounds of general formula (I) according to the present invention and the salts thereof can be administered enterally or parenterally in liquid or solid form. For this purpose, there can be used all conventional forms of administration, for example tablets, capsules, dragees, syrups, solutions, suspensions and the like. As injection medium, it is preferred to use water which contains the additives usual in the case of injection solutions, for example stabilising agents, solubilising agents and buffers. Additives of this kind include, for example, tartrate and citrate buffers, ethanol, complex formers (such as ethylenediaminetetraacetic acid and the non-toxic salts thereof) and high molecular weight polymers (such as liquid polyethylene oxide) for viscosity regulation. Liquid carrier materials for injection solutions must be sterile and are preferably placed in ampoules. Solid carrier materials include, for example, starch, lactose, mannitol, methyl cellulose, talc, highly dispersed silicic acids, high molecular weight fatty acids (such as stearic acid), gelatine, agar agar, calcium phosphate, magnesium stearate, animal and vegetable fats and solid high molecular weight polymers (such as polyethylene glycol). Compositions suitable for oral administration can, if desired, also contain flavouring and sweetening agents.

The dosage can depend upon various factors, such as the mode of administration, species, age and/or individual condition. The dosages to be administered daily are about 1 to 1000 mg. in the case of humans and preferably 10 to 200 mg. and can be given once or several times per day.

Preferred compounds according to the present invention are, apart from the compounds mentioned hereinafter in the specific Examples and apart from the compounds which can be derived by combination of all of the meanings given in the claims, the following diphosphonates, as well as the methyl and ethyl esters thereof:

1-amino-3-(N-methyl-N-nonylamino)-propane-1,1-diphosphonic acid 1-dimethylamino-3-(N-methyl-N-nonylamino)-propane-1,1-diphosphonic acid 3-(N-methyl-N-nonylamino)-propane-1,1-diphosphonic acid 3-(N-methyl-N-octadecylamino)-propane-1-hydroxy-1,1-diphosphonic acid 3-(N-methyl-N-tetradecylamino)-propane-1-hydroxy-1,1-diphosphonic acid 3-(N-decyl-N-methylamino)-propane-1-hydroxy-1,1-diphosphonic acid 3-(N-heptyl-N-methylamino)-propane-1-hydroxy-1,1-diphosphonic acid 1-hydroxy-4-methyl-4-(N-nonyl-N-methylamino)-butane-1,1-diphosphonic acid 4-(N-dodecyl-N-methylamino)-butane-1-hydroxy-1,1-diphosphonic acid 3-(N-dodecyl-N-isopropylamino)-propane-1-hydroxy-1,1-diphosphonic acid 1-hydroxy-5-methyl-5-(N-nonyl-N-methylamino)-
pentane-1,1-diphosphonic acid 1-[hydroxy-3-(N-cyclohexylmethyl)-N-
propylamino]-propane-1,1-diphosphonic acid 2-(N-methyl-N-isobutylamino)-ethane-1,1-diphosphonic acid 2-(N-methyl-N-pentylamino)-ethane-1,1-diphosphonic acid.

The following Examples illustrate some of the process variants which can be used for the synthesis of the compounds according to the present invention. The structures of these compounds were verified by H—and P—NMR spectroscopy and the purity by means of P—NMR spectroscopy, thin layer electrophoresis (cellulose, oxalate buffer of pH 4.0) and by means of C, H, N, P and Na analyses. For the characterisation of the individual compounds, there are given the $M_{rel}$ values (relative mobilities) referred to pyrophosphate ($M_{rel}=1.0$).

EXAMPLE 1

1-Hydroxy-3-(N,N-dipentylamino)-propane-1,1-diphosphonic acid 13.3 g. 3-N,N-Dipentylaminopropionic acid are kept for 20 hours at 100° C. with 7.1 g. phosphorous acid and 14.8 ml. phosphorus trichloride in 67 ml. chlorobenzene. The solvent is then decanted off and the residue is stirred under reflux with 180 ml. 6N hydrochloric acid for 8 hours. Insoluble material is filtered off and the filtrate is concentrated and applied to a column of Amberlite IR 120 (H+ form). The elution with water is monitored electrophoretically. The desired fractions are combined, evaporated and stirred up with acetone and the crystals obtained are isolated. There are thus obtained 12.9 g. of crude product. After recrystallising twice from water, there are obtained 4.7 g. (22% of theory) of analytically pure product in the form of the hemihydrate; m.p. 114° C. with sintering, 189°–191° C. (decomp.); $M_{rel}=0.24$.

The starting material is obtained as follows: Dipentylamine is reacted with methyl acrylate in toluene in the mole ratio of 1:3. There is obtained a yield of 28% of theory of the oily dipentylaminopropionic acid ester which is saponified with 1N aqueous sodium hydroxide solution to give a yield of 56% of theory of the desired acid; m.p. 47°–49° C.

EXAMPLE 2

1-Hydroxy-3-(N-methyl-N-nonylamino)-propane-1,1-diphosphonic acid

In a manner analogous to that described in Example 1, from 3-N-methyl-N-nonylaminopropionic acid there is obtained the corresponding diphosphonate in a yield of 10% of therory; m.p. 159° C. with sintering, 178°–184° C.; $M_{rel}=0.22$.

The starting material is obtained as follows: Nonylamine is reacted with benzaldehyde to give the oily Schiff base in a yield of 96% of theory. Hydrogenation with palladium-charcoal catalyst gives N-benzyl-N-nonylamine as an oil in a yield of 94% of theory. From this, with formaldehyde and formic acid, there is obtained the oily N-benzyl-N-methyl-N-nonylamine in a yield of 98% of theory. Hydrogenolytic splitting off of the benzyl radical with palladium-charcoal catalyst gives a quantitative yield of the secondary amine in the form of an oil which is reacted with methyl acrylate and saponified in the manner described in Example 1. The yield of the oily ester is 81% of theory and that of the pasty acid is 95% of theory.

EXAMPLE 3

3-(N-Cyclohexyl-N-methylamino)-1-hydroxy-propane-1,1-diphosphonic acid.

15 g. 3-N-Cyclohexyl-N-methylaminopropionic acid (prepared from N-cyclohexyl-N-methylamine (commercially available) and methyl acrylate in toluene; yield of ester 76% of theory, m.p. 131°–134° C., yield of acid 92% of theory, m.p. 101°–105° C.) are heated to 80° C. with 13.3 g. phosphorous acid. The melt is mixed with 14.1 ml. phosphorus trichloride and kept at the same temperature for 16 hours. 240 ml. water are then added thereto and the reaction mixture is stirred for 1 day at 100° C. It is then filtered, the filtrate is concentrated in a vacuum and the oil obtained is poured into 1 litre of acetone, crystallisation thereby commencing. The crystals are dissolved in water and purified by ion exchanger chromatography in the manner described in Example 1. Yield 4.5 g. (16.9% of theory) as monohydrate; m.p. 142° C. with sintering, 182° C. (decomp.); $M_{rel}=0.3$.

EXAMPLE 4

1 g. 3-N-Cyclohexylaminopropane-1-hydroxy-1,1-diphosphonic acid is suspended in 30 ml. methylene chloride, 2.5 ml. of a concentrated aqueous solution of sodium hydroxide are added thereto and, with cooling, mixed with 1 g. tetrabutylammonium hydrogen sulphate and 0.3 ml. dimethyl sulphate. The reaction mixture is then vigorously stirred for several hours at ambient temperature. After working up in the usual manner, the identity of the product obtained with that prepared according to Example 3 is demonstrated by mass spectroscopy after silylation.

The diphosphonic acid used as starting material is obtained as follows: Cyclohexylamine is reacted with acrylic acid in pyridine to give a yield of 70% of theory of 3-N-cyclohexylaminopropionic acid; m.p. 170°–171° C. The reaction with phosphorous acid and phosphorus trichloride gives a yield of 31% of theory of the diphosphonic acid; m.p. 164° C. (decomp.).

EXAMPLE 5

3-(N-Cyclohexylmethyl-N-methylamino)-propane-1-hydroxy-1,1-diphosphonic acid 3-(N-Cyclohexylmethyl-N-methylamino)-propionic acid (prepared from N-benzyl-N-methylamine by hydrogenation with platinum catalyst, yield 70% of theory; b.p. 60° C./16 mm.Hg; reaction with methyl acrylate in toluene, yield 37% of theory of methyl 3-(N-cyclohexylmethyl-N-methylamino)-propionate; saponification with 1N aqueous sodium hydroxide solution to give the acid in a yield of 63% of theory; m.p. 98°–102° C.) is reacted analogously to Example 3 with phosphorous acid/phosphorus trichloride to give the diphosphonic acid in a yield of 34% of theory; m.p. 180°–194° C. (decomp.); $M_{rel}=0.31$.

EXAMPLE 6

1-Hydroxy-3-(N-nonyl-N-propylamino)-propane-1,1-diphosphonic acid

In a manner analogous to that described in Example 3, from 3-N-nonyl-N-propylaminopropionic acid there is obtained the corresponding diphosphonic acid in a yield of 50% of theory; m.p. 100°–105° C.; $M_{rel}=0.23$.

The starting material is obtained as follows: 2 mole nonylamine are reacted with 1 mole propionyl chloride to give a quantitative yield of the acid amide which is reduced with lithium aluminium hydride to give the secondary amine in a yield of 71% of theory; b.p. 113°–117° C./16 mm.Hg. 1 mole N-nonyl-N-propylamine is reacted with 3 mole methyl acrylate in toluene to give an oil in a yield of 81% of theory which is saponified with 1N aqueous sodium hydroxide solution to give the desired acid in a yield of 14% of theory; m.p. 45°–47° C.

EXAMPLE 7

500 mg. of the diphosphonic acid prepared according to Example 1 are suspended in 5 ml. water, dissolved with 2.68 ml. 1N aqueous sodium hydroxide solution, concentrated somewhat and brought to crystallisation by pouring into acetone. There are thus obtained 440 mg. (78% of theory) of the disodium salt of 1-hydroxy-3-(N,N-dipentylamino)-propane-1,1-diphosphonic acid in the form of the monohydrate. The melting point is above 300° C.

EXAMPLE 8

1-Hydroxy-3-(N-nonyl-N-pentylamino)-propane-1,1-diphosphonic acid 2 mole nonylamine are reacted with 1 mole valeroyl chloride in diethyl ether, the suspension is filtered off with suction, the filtrate is evaporated and N-nonyl-valeric acid amide is thus obtained quantitatively; m.p. 29°–31° C. Reduction with 1.65 mole lithium aluminium hydride in diethyl ether gives a colourless oil in a yield of 78% of theory; b.p. 142°–146° C./16 mm.Hg. The addition of this N-nonyl-N-pentylamine to methyl acrylate (oil; yield 96% of theory) and subsequent saponification with 1N aqeuous sodium hydroxide solution gives a yield of 64% of theory of pasty 3-(N-nonyl-N-pentylamino)-propionic acid which is reacted analogously to Example 3 to give the diphosphonic acid; yield 87% of theory; m.p. 168°–176° C.; $M_{rel}=0.14$.

EXAMPLE 9

In a manner analogous to that described in Example 2, there are prepared:

| A. Intermediate products: | yield | m.p. |
|---|---|---|
| N-benzylidenepentylamine | 94% | oil |
| N-benzyl-N-pentylamine | 74% | paste |
| N-benzyl-N-methyl-N-pentylamine | 95% | oil |
| N-methyl-N-pentylamine | 49% | oil |
| methyl 3-(N-methyl-N-pentylamino)-acrylate | 93% | oil |
| 3-(N-methyl-N-pentylamino)-propionic acid | 34% | deliquescent crystals |
| End product: | | |
| 1-hydroxy-3-(N-methyl-N-pentylamino)-propane-1,1-diphosphonic acid | $M_{rel}=$ 0.44 | 84° C. decomp. |

| B. Intermediate products: | | |
|---|---|---|
| N-benzylideneisobutylamine | 96% | oil |
| N-benzyl-N-isobutylamine | 71% | oil |
| N-benzyl-N-isobutyl-N-methylamine | 93% | oil |
| N-isobutyl-N-methylamine | 96% | oil |
| methyl 3-(N-isobutyl-N-methylamino)-acrylate | 90% | oil |
| 3-(N-isobutyl-N-methylamino)-propionic acid | 57% | oil |
| End product: | | |
| 1-hydroxy-3-(N-isobutyl-N-methylamino)-propane-1,1-diphosphonic acid | $M_{rel}=$ 0.40 yield 39% | m.p. 140° C. decomp. |

| C. Intermediate products: | | |
|---|---|---|
| N-benzylidenehexadecylamine | 85% | oil |
| N-benzyl-N-hexadecylamine | 76% | wax |
| N-benzyl-N-hexadecyl-N-methylamine | 93% | oil |
| N-hexadecyl-N-methylamine | 98% | wax |
| methyl 3-(N-hexadecyl-N-methylamino)-acrylate | 100% | wax |
| 3-(N-hexadecyl-N-methylamino)-propionic acid | 37% | 58–60° C. |
| End product: | | |
| 3-(N-hexadecyl-N-methylamino)-propane-1-hydroxy-1,1-diphosphonic acid | $M_{rel}=$ 0.1 72% | 198–254° C. decomp. |

The oily intermediate products are further reacted without distillation. The purification of the end products is carried out by ion exchange chromatography.

EXAMPLE 10

3-N,N-Dinonylaminopropane-1-hydroxy-1,1-diphosphonic acid

In a manner analogous to that described in Example 3, from 3-N,N-dinonylaminopropionic acid there is obtained the corresponding diphosphonic acid as the hemihydrate in a yield of 49% of theory; m.p. 83° C. sinters, 161°–171° C. melts with gas evolution; $M_{rel}=0.16$.

The reaction sequence for the preparation of the starting material is analogous to that described in Example 6:

| pelargonic acid N-nonylamide; | yield 100% of theory: m.p. 52–55° C. |
|---|---|
| N,N-dinonylamide; | yield 79% of theory; m.p. 37–39° C. |
| methyl 3-N,N-dinonylaminopropionate; | yield 71% of theory; oil |
| 3-N,N-dinonylaminopropionic acid; | yield 18% of theory; deliquescent crystals. |

EXAMPLE 11

1-Hydroxy-4-(N,N-di-3-methylbutylamino)-butane-1,1-diphosphonic acid 4 g. 4-Amino-1-hydroxybutane-1,1-diphosphonic acid are dissolved in 64 ml. 1N aqueous sodium hydroxide solution, mixed with 3.8 ml. isovaleraldehyde and, after the addition of 2.5 g. of 10% palladium-charcoal, hydrogenated at a pressure of 5 bar. The course of the reaction is monitored electrophoretically until the starting material has disappeared. The reaction mixture is filtered, acidified with Amberlite R 120 (H+ form) and evaporated until crystallisation commences, 1.3 g. of crystals thus being obtained in a yield of 20% of theory; m.p. 225°–227° C. (decomp.); $M_{rel}=0.39$. 1-Hydroxy-4-(N-3-methylbutylamino)-butane-1,1-diphosphonic acid remaining in the mother liquor, which is formed as an intermediate, can be used again for the reductive alkylation.

EXAMPLE 12

3-(N-Benzyl-N-methylamino)-propane-1-hydroxy-1,1-diphosphonic acid

Analogously to Example 3, from 3-N-benzyl-N-methylaminopropionic acid there is obtained the desired diphosphonic acid as monohydrate in a yield of 36% of theory; decomposition point 117° C.; $M_{rel}=0.37$.

The starting material is obtained as follows: N-Benzyl-N-methylamine is reacted with methyl acrylate analogously to Example 1 and the ester obtained in a yield of 76% of theory is, without distillation, saponified with 1N aqueous sodium hydroxide solution. The oily acid is thus obtained in a yield of 67% of theory and is used without further purification.

EXAMPLE 13

3-(N-Dodecyl-N-methylamino)-propane-1-hydroxy-1,1-diphosphonic acid

Analogously to Example 3, from 3-N-dodecyl-N-methylaminopropionic acid there is obtained the desired compound in a yield of 28% of theory; decomposition point 200°–216° C.; $M_{rel}=0.1$.

The starting material is obtained as follows: The oily Schiff base obtained from dodecylamine and benzaldehyde (yield 81% of theory) is hydrogenated with palladium catalyst to give the oily N-benzyl compound in a yield of 74% of theory. The reductive alkylation with formalin-formic acid gives the tertiary amine, which is also oily, in a yield of 82% of theory. The catalytic removal of the benzyl radical by hydrogenolysis is quantitative. The oily secondary amine is reacted directly with methyl acrylate to give a pasty product in a yield of 50% of theory which is saponified without purification. The desired acid is obtained as a viscous mass in a yield of 39% of theory and is used directly.

EXAMPLE 14

3-(N-Benzyl-N-propylamino)-propane-1-hydroxy-1,1-diphosphonic acid

Analogously to Example 3, from 3-(N-benzyl-N-propylamino)-propionic acid there is obtained the desired compound in a yield of 35% of theory; m.p. 112°–115° C. (decomp.); $M_{rel}=0.33$.

The starting material is obtained as follows: The oily Schiff base from propylamine and benzaldehyde (yield 86% of theory) is hydrogenated in the presence of palladium catalyst and gives N-benzyl-N-propylamine in a yield of 81% of theory. The oily secondary amine is now reacted with methyl acrylate to give the oily ester in a yield of 69% of theory from which, by alkaline saponification, there is obtained the acid, which is also an oil, in a yield of 88% of theory.

EXAMPLE 15

In a manner analogous to that described in Example 2, there are prepared:

| A. Intermediate products: | yield | m.p. |
|---|---|---|
| N-benzylidene-2-butylamine | 89% | oil |
| N-benzyl-2-butylamine | 92% | oil |
| N-benzyl-N-2-butyl-N-methylamine | 85% | oil |
| N-2-butyl-N-methylamine, HCl | 98% | 40–46° C. |
| methyl 3-(N-2-butyl-N-methylamino)-propionate | 88% | oil |
| 3-(N-2-butyl-N-methylamino)-propionic acid | 95% | oil |
| End product: | | |
| 3-(N-2-butyl-N-methylamino)-propane-1-hydroxy-1,1-diphosphonic acid | 39% | 95–105° C. |

| B. Intermediate products: | | |
|---|---|---|
| methyl 3-N-butylaminopropionate; b.p. 95–100° C./20 mm.Hg | 75% | oil |
| methyl 3-(N-butyl-N-methylamino)-propionate | — | oil |
| 3-(N-butyl-N-methylamino)-propionic acid (yield referred to first intermediate product) | 78% | oil |
| End product: | | |
| 3-(N-butyl-N-methylamino)-propane-1-hydroxy-1,1-diphosphonic acid $M_{rel} = 0.39$ | 65% | 116–121° C. |

| C. Intermediate product: | | |
|---|---|---|
| 4-(N-methyl-N-nonylamino)-butyric acid | 47% | oil |
| End product: | | |
| 1-hydroxy-4-(N-methyl-N-nonylamino)-butane-1,1-diphosphonic acid disodium salt dihydrate $M_{rel} = 0.25$ | 11% | 300° C. |

| D. Intermediate products: | | |
|---|---|---|
| 3-N-undecylaminopropionic acid | 62% | 76–80° C. |
| 3-N-methyl-N-undecylaminopropionic acid | 59% | wax |
| End product: | | |
| 1-hydroxy-3-N-methyl-N-undecylamino)-propane-1,1-diphosphonic acid dipotasium salt dihydrate | 23% | 238° C. foaming up |

The oily intermediate products are further reacted directly without distillation. The structure is verified spectroscopically. The end products are purified by ion exchanger chromatography.

EXAMPLE 16

Test Report

Male Wistar rats from our own breeding weighing about 160 g were thyroparathyroidectomized on day 1. On day 5, the success of the operation was controlled by measuring calcemia after a night fasting. From that day on, all the animals were group-fed, that means all of them ate the same quantity of food. Furthermore, the animals received then daily for 3 days 2 subcutaneous injections, one containing 25 µg of a synthetic retinoid, the other one the bisphosphonate to be tested. Additionally, all animals were given 2 µg of thyroxine the first and last day of treatment. 24 h after the last injection of the retinoid and the biphosphonates and after one night fasting, blood was taken by retroorbital puncture under ether anesthesia. Plasma calcium was then analyzed by means of atomic absorption.

The bisphosphonates were given first at a dose of 0.1 mg P/kg in a volume of 2 ml/kg, the less active also at 1 and 10 mg P/kg.

TABLE I

Depression of hypercalcemia (in mg %) at various dosages of the diphosphonate compounds administered

| Examples | dosage [mg P/kg] | | |
|---|---|---|---|
| | 0.01 | 0.1 | 1 |
| 2 | 1.75 | 5.74 | |
| 6 | | 2.26 | 5.90 |
| 8 | | 0.49 | 1.74 |
| 9A | 4.59 | 7.34 | |
| 9B | 3.36 | 6.06 | |
| 12 | 0.69 | 4.34 | |
| 15A | 1.43 | 3.12 | |

It will be understood that the specification and examples are illustrative but not limitative of the present invention and that other embodiments within the spirit and scope of the invention will suggest themselves to those skilled in the art.

What is claimed:

1. A diphosphonate compound of the formula:

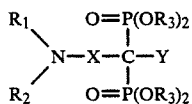

2. A diphosphonate compound of claim 1, wherein $R_1$ is methyl.

3. The diphosphonate compound of claim 1 designated 1-hydroxy-3-(N-methyl-N-nonylamino)-propane-1,1-diphosphonic acid and the physiologically active salt thereof.

4. The diphosphonate compound of claim 1 designated 1-hydroxy-3-(N-methyl-N-pentylamino)-propane-1,1-diphosphonic acid and the physiologically active salt thereof.

5. The diphosphonate compound of claim 1 designated 1-hydroxy-3-(N-isobutyl-N-methylamino)-propane-1,1-diphosphonic acid and the physiologically active salt.

6. A method for the treatment or prophylaxis of calcium metabolism disturbance or disease comprising administering a pharmaceutically effective amount of the compound of claim 1.

7. The method of claim 6 wherein 0.01–10 mg P/kg of the pharmaceutically acceptable diphosphonate compound are administered per day.

8. A method for the treatment or prophylaxis of calcium metabolism disturbance or disease comprising administering a pharmaceutically effective amount of at least one of the compounds designated 1-hydroxy-3-(N-methyl-N-nonylamino)-propane-1,1-diphosphonic acid, 1-hydroxy-3-(N-methyl-N-pentylamino)-propane-1,1-diphosphonic acid and 1-hydroxy-3-(N-isobutyl-N-methylamino)-propane-1,1-diphosphonic acid.

9. The method of claim 8 wherein 0.01–10 mg P/kg of the pharmaceutically acceptable disphosphonate are administered per day.

10. A pharmaceutical composition for the treatment or prophylaxis of calcium metabolism disturbance or disease containing an effective amount of at least one compound of claim 1 in a pharmaceutically acceptable carrier.

11. A pharmaceutical composition for the treatment or prophylaxis of calcium metabolism disturbance or disease containing an effective amount of at least one compound of claim 2 in a pharmaceutically acceptable carrier.

12. A pharmaceutical composition for the treatment or prophylaxis of calcium metabolism disturbance or disease containing an effective amount in a pharmaceutically acceptable carrier of at least one compound designated 1-hydroxy-3-(N-methyl-N-nonylamino)-propane-1,1-diphosphonic acid, 1-hydroxy-3-(N-methyl-N-pentylamino)-propane-1,1-diphosphonic acid, and 1-hydroxy-3-(N-isobutyl-N-methylamino)-propane-1,1-diphosphonic acid.

* * * * *

UNITED STATES PATENT AND TRADEMARK OFFICE
CERTIFICATE OF CORRECTION

PATENT NO.  : 4,927,814
DATED       : May 22, 1990
INVENTOR(S) : Rudi Gall et al.

It is certified that error appears in the above-identified patent and that said Letters Patent is hereby corrected as shown below:

Column 13, line 29, after formula insert: wherein $R_1$ is methyl or n-propyl which is optionally substituted by phenyl or cyclohexyl, $R_2$ is isobutyl, pentyl, nonyl or benzyl wherein said aliphatic hydrocarbon is optionally substituted by phenyl or oxygen, and wherein said oxygen is an ester or an ether, $R_3$ is hydrogen, X is ethylene, and Y is hydroxyl; and the pharmacologically acceptable salt thereof.

Signed and Sealed this

Twelfth Day of January, 1993

Attest:

DOUGLAS B. COMER

Attesting Officer

Acting Commissioner of Patents and Trademarks